US008187630B2

(12) United States Patent
Cho

(10) Patent No.: US 8,187,630 B2
(45) Date of Patent: May 29, 2012

(54) EXTENDED RELEASE ORAL DOSAGE COMPOSITION

(75) Inventor: Wing-Kee Philip Cho, Princeton, NJ (US)

(73) Assignee: Schering-Plough Corporation, Kenilworth, NJ (US)

( * ) Notice: Subject to any disclaimer, the term of this patent is extended or adjusted under 35 U.S.C. 154(b) by 369 days.

(21) Appl. No.: 12/573,022

(22) Filed: Oct. 2, 2009

(65) Prior Publication Data

US 2010/0021542 A1 Jan. 28, 2010

Related U.S. Application Data

(60) Division of application No. 10/699,987, filed on Nov. 3, 2003, which is a continuation of application No. 10/175,480, filed on Jun. 19, 2002, now Pat. No. 6,709,676, which is a continuation-in-part of application No. PCT/US00/34404, filed on Dec. 19, 2000.

(60) Provisional application No. 60/172,752, filed on Dec. 20, 1999.

(51) Int. Cl.
*A61K 9/58* (2006.01)
*A61K 9/20* (2006.01)
*A61K 9/22* (2006.01)
*A61K 9/24* (2006.01)

(52) U.S. Cl. ........ 424/462; 424/464; 424/465; 424/468; 424/472

(58) Field of Classification Search .................. None
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 3,940,485 A | 2/1976 | Levinson et al. |
| 4,008,796 A | 2/1977 | Aylon |
| 4,282,233 A | 8/1981 | Vilani |
| 4,371,516 A | 2/1983 | Gregory et al. |
| 4,552,899 A | 11/1985 | Sunshine et al. |
| 4,659,716 A | 4/1987 | Villani et al. |
| 4,731,447 A | 3/1988 | Schumacher et al. |
| 4,777,170 A | 10/1988 | Heinrich |
| 4,783,465 A | 11/1988 | Sunshine et al. |
| 4,804,666 A | 2/1989 | Piwinski et al. |
| 4,863,931 A | 9/1989 | Schumacher et al. |
| 4,906,647 A | 3/1990 | Kouchiwa et al. |
| 4,917,900 A | 4/1990 | Jones et al. |
| 4,990,535 A | 2/1991 | Cho et al. |
| 5,019,591 A | 5/1991 | Gardner et al. |
| 5,089,496 A | 2/1992 | Piwinski et al. |
| 5,100,675 A | 3/1992 | Cho et al. |
| 5,314,697 A | 5/1994 | Kwan et al. |
| 5,407,941 A | 4/1995 | Carceller et al. |
| 5,476,856 A | 12/1995 | Carceller et al. |
| 5,487,901 A | 1/1996 | Conte et al. |
| 5,508,042 A | 4/1996 | Oshlack et al. |
| 5,595,997 A | 1/1997 | Aberg et al. |
| 5,731,319 A | 3/1998 | Aberg et al. |
| 5,900,421 A | 5/1999 | Handley et al. |
| 5,939,426 A | 8/1999 | McCullough |
| 5,962,464 A | 10/1999 | Handley et al. |
| 5,997,903 A | 12/1999 | Dietrich et al. |
| 6,051,585 A | 4/2000 | Weinstein et al. |
| 6,100,274 A | 8/2000 | Kou |
| 6,114,346 A | 9/2000 | Harris et al. |
| 6,132,758 A | 10/2000 | Munayyer et al. |
| 6,265,414 B1 | 7/2001 | Harris et al. |
| 6,270,796 B1 | 8/2001 | Weinstein |
| 6,372,802 B2 | 4/2002 | Hellberg et al. |
| 6,423,721 B1 | 7/2002 | Harris et al. |
| 6,432,972 B2 | 8/2002 | Salmun et al. |
| 6,506,767 B1 | 1/2003 | Schumacher et al. |
| 6,514,520 B2 | 2/2003 | Munayyer et al. |
| 6,521,254 B2 | 2/2003 | Weinstein et al. |
| 6,599,913 B1 | 7/2003 | Johnson et al. |
| 6,709,676 B2 | 3/2004 | Cho |
| 6,979,463 B2 | 12/2005 | Kou |
| 7,211,582 B1 | 5/2007 | Aberg et al. |
| 7,214,683 B1 | 5/2007 | Aberg et al. |
| 7,214,684 B2 | 5/2007 | Aberg et al. |
| 7,405,223 B2 | 7/2008 | Affrime et al. |
| 7,618,649 B2 | 11/2009 | Cho |

(Continued)

FOREIGN PATENT DOCUMENTS

EP 0 264 259 A1 4/1988

(Continued)

OTHER PUBLICATIONS

Connors, et al., Chemical Stability of Pharmaceuticals, a Handbook for Pharmacists, 135-159 (John Wiley & Sons 1986).
Technology of Drug Forms, Educational Literature for Students of Pharmaceutical Institutes, vol. 2, 134, 187, 188, 189 (L.A. Ivanova, ed.) (Moscow, "Meditsina" 1991).
Food and Drug Administration / Center for Drug Evaluation and Research, Guidance for Industry—Q3B Impurities in New Drug Products (Nov. 1997).
Food and Drug Administration / Center for Drug Evaluation and Research, Guidance for Industry—Dissolution Testing of Immediate Release Solid Oral Dosage Forms (Aug. 1997).

(Continued)

*Primary Examiner* — Robert A Wax
*Assistant Examiner* — Randeep Singh
(74) *Attorney, Agent, or Firm* — Matthew A. Leff; Valerie J. Camara

(57) ABSTRACT

A bilayer solid composition comprising (a) an immediate release first layer comprising an anti-allergic effective amount of desloratadine and at least one pharmaceutically acceptable excipient and (b) a sustained release second layer comprising an effective amount of a nasal decongestant, e.g. pseudoephedrine sulfate and a pharmaceutically acceptable sustained release agent wherein the composition contains less than about 2% of desloratadine decomposition products is disclosed. A solid composition comprising an anti-allergic effective amount of desloratadine and at least one, and preferably two pharmaceutically acceptable antioxidants is also disclosed.

29 Claims, No Drawings

U.S. PATENT DOCUMENTS

| | | |
|---|---|---|
| 2002/0123504 A1 | 9/2002 | Redmon et al. |
| 2004/0097536 A1 | 5/2004 | Cho |
| 2006/0079489 A1 | 4/2006 | Redmon et al. |

FOREIGN PATENT DOCUMENTS

| | | |
|---|---|---|
| EP | 0 288 640 A1 | 11/1988 |
| EP | 0173928 B1 | 6/1990 |
| EP | 0 396 404 A1 | 11/1990 |
| EP | 0 577 957 A1 | 1/1994 |
| EP | 0 396 404 B1 | 12/1994 |
| EP | 0655744 B1 | 1/2000 |
| EP | 1112738 A2 | 7/2001 |
| WO | WO-85/03707 A1 | 8/1985 |
| WO | WO-92/00293 A1 | 1/1992 |
| WO | WO-92/11034 A1 | 7/1992 |
| WO | WO-92/20377 A1 | 11/1992 |
| WO | WO-94/09761 A1 | 5/1994 |
| WO | WO-96/16641 A1 | 6/1996 |
| WO | WO-96/20708 A1 | 7/1996 |
| WO | WO-98/34614 A1 | 8/1998 |
| WO | WO-00/02560 A1 | 1/2000 |

OTHER PUBLICATIONS

Food and Drug Administration / Center for Drug Evaluation and Research, Guidance for Industry—SUPAC-MR: Modified Release Solid Oral Dosage Forms, Scale-Up and Postapproval Changes: Chemistry, Manufacturing, and Controls; In Vitro Dissolution Testing and In Vivo Bioequivalance Documentation (Sep. 1997).

International Conference on Harmonisation of Technical Requirements for Registration of Pharmaceuticals for Human Use, ICH Harmonised Tripartite Guideline—Impurities in New Drug Prodcuts Q3B(R2), Current Step 4 Version (Jun. 2, 2006).

USP 30 / NF 25, vol. 1, 277-284 (2007).

Andersen, et al., "Adverse drug interactions clinically important for the dermatologist," Arch Dermatol, Apr. 1995, vol. 131, pp. 468-473.

Babe, et al., "Histamine, Bradykinn, and their Antagonists" in The Pharmacological Basis of Therapeutics (9th edition), The McGraw-Hill Co. Inc., 1996, pp. 581-599.

Barnett, et al., "Pharmacology of Non-Sedating H1 Antihistamines," New Perspectives in Histamine Research, Birkhauser Verlag Basel, 1991, pp. 181-196.

Berge, et al., "Pharmaceutical Salts," J. of Pharm. Sciences, Jan. 1977, vol. 66, No. 1, pp. 1-19.

Berthon, et al., "In Vitro inhibition, by loratadine and descarboxyethoxyloratadine, of histamine release from human basophils, and of histamine release and intracellular calcium fluxes in rat basophilic leukemia cells (RBL-2H3)," Biochem. Pharm., 1994, vol. 47, No. 5, pp. 789-794.

Blaug, et al., "Interaction of dextroamphetamine sulfate with spray-dried lactose," J. of Pharm. Sciences, Nov. 1972, vol. 61, No. 11, pp. 1770-1775.

Brandes, et al., "Enhanced cancer growth in mice administered daily human-equivalent doses of some H1-antihistamines: predictive in vitro correlates," J. of the National Cancer Inst., May 18, 1994, vol. 86, No. 10, pp. 770-775.

Brandes, et al., "Stimulation of malignant growth in rodents by antidepressant drugs at clinically relevant doses," Cancer Research, Jul. 1, 1992, vol. 52, pp. 3796-3800.

Brion et al., "Evaluation of the antimuscarinic activity of atropine, terfenadine and mequitazine in healthy volunteers," Br. J. Clin. Pharmac. 1988, vol. 25, pp. 27-32.

Carmeliet, "Voltage- and Time-Dependent Block of the Delayed K+ Current in Cardiac Myocytes by Dofetilide," The J. of Pharm. and Experimental Therapeutics, 1992, vol. 262, No. 2, pp. 809-817.

Castello, et al., "Discloration of tablets containing amines and lactose," J. of Pharm. Sciences, Feb. 1962, vol. 51, No. 2, pp. 106-108.

Cheung, et al., "Investigation of anti-motion sickness drugs in the squirrel monkey," J. Clin. Pharmacol, 1992, vol. 32, pp. 163-175.

Clissold, et al., "Loratadine: A preliminary review of its pharmacodynamic properties and therapeutic efficacy," Drugs, 1989, vol. 37, pp. 42-57.

Cooke, "Glycopyrrolate in bladder dysfunction," SA Medical Journal, Jan. 1, 1986, p. 3.

Craft, "Torsade de pointes after astemizole overdose," Br. Medical Journal, 1986, vol. 292, p. 660.

Dorje, et al., "Antagonist Binding Profiles of Five Cloned Human Muscarinic Receptor Subtypes," The J. of Pharm. and Experimental Therapeutics, 1991, vol. 256, pp. 727-733.

Drug Facts and Comparison, 1998, Ed., Facts and Comparisons, St. Louis, Missouri, p. 2832.

Ebert, "Soft elastic gelatin capsules: a unique dosage form," Pharmaceutical Technology, 1977, pp. 44-50.

Gengo, "Dilemma: Antihistamine selection: Use vs. Side effects," U.S. Pharmacist, Nov. 1990, pp. 59-92.

Hartauer, et al., "A Comparison of Diffuse Reflectance FT-IR Spectroscopy and DSC in the Characterization of a Drug-Excipient Interaction,"Drug Development and industrial Pharmacy, 1991, vol. 17, No. 4, pp. 617-630.

Herron, et al., "Dose Proportionality, Linearity, and Pharmacokinetics of Desloratadine in Healthy Volunteers" (Abstract 1126), J. Allergy Clin. Immunol., Jan. 2000, vol. 105, No. 1, Part 2, p. S385.

Herzog, et al., "Urinary Incontinence: Medical and Psychosocial Aspects," Annual Review of Gerontology and Geriatrics, 1989, vol. 9, pp. 74-119.

Hilbert, et al., "Pharmacokinetics and Dose Proportionality of Loratadine," J. Clin. Pharmacol., 1987, vol. 27, pp. 694-698.

Housley, et al., "Histamine and related substances influence neurotransmission in the semicircular canal," Hearing Research, May 1, 1988, vol. 35, pp. 87-97.

Jankowski, et al., "Effect of Terfenadine on Nasal Provocation," Int. Arch. Allergy Immunolog., 1993, vol. 101, pp. 311-317.

Kaliner, "Nonsedating Antihistamines: Pharmacology, Clinical Efficacy and Adverse Effects," American Family Physician, Mar. 1992, vol. 45, No. 3, pp. 1337-1342.

Kleine-Tebbe, et al., "Inhibition of IgE- and non-IgE-mediated histamine release from human basophil leukocytes in vitro by a histamine H1-antagonist, desethoxycarbonyl-loratadine," J. Allergy Clin. Immunol., 1994, vol. 93, pp. 494-500.

Knowles, "Astemizole and Terfenadine-Induced Cardiovascular Effects," The Canadian J. of Hospital Pharmacy, Feb. 1992, vol. 45, No. 1, pp. 33 and 37.

Kohl, et al., "Lack of Effects of Astemizole on Vestibular Ocular Reflex, Motion Sickness, and Cognitive Performance in Man," Aviation, Space, and Environmental Medicine, Dec. 1987, pp. 1171-1174.

Kohl, et al., "New Pharmacologic Approaches to the Prevention of Space/Motion Sickness," J. Clin. Pharmocol, 1991, vol. 31, pp. 934-946.

Kohl, et al., "Control of Nausea and autonomic dysfunction with terfenadine, a peripherally acting antihistamine," Aviation, Space and Environmental Medicine, May 1991, pp. 392-396.

Kreutner, et al., "Profile of Desloratadine as a Selective and Non-Sedating Histamine H1-Receptor Antagonist," Preclinical Efficacy and Antiallergic, J. Allergy Clin. Immunol. (Abstract 1118), 2000, vol. 105, No. 1, part 2, pp. S382-S383.

Kubo, et al., "Antimuscarinic Effects of Antihistamines: Quantitative Evaluation by Receptor-Binding Assay," Japan J. Pharmacol., 1987, vol. 43, pp. 277-282.

Lathers, et al., "Pharmacology in space: Part 2. Controlling motion sickness," TiPS, Jun. 1989, vol. 10, pp. 243-250.

Levin, et al., "Direct Measurement of the Anticholinergic Activity of a Series of Pharmacological Compounds on the Canine and Rabbit Urinary Bladder," The J. of Urology, Aug. 1982, vol. 128, pp. 396-398.

Lunde, "Antihistamines," Side Effects of Drugs Annual 14, Elsevier Science Publishers B.V., 1990, pp. 135-138.

Lunde, "Antihistamines," Side Effects of Drugs Annual 12; A Worldwide Yearly Survey of New Data and Trends, Elsevier Science Publishers B.V., 1998, pp. 142-143.

Massad, et al., "The Pharmacokinetics of Intravesical and Oral Oxybutynin Chloride," The J. of Urology, Aug. 1992, vol. 148, pp. 595-597.

McCue, Safety of Antihistamines in the Treatment of Allergic Rhinitis in Elderly Patients, Arch., Fam. Med. Sep. 1996, vol. 5, pp. 464-468.

Miadonna, et al., "Inhibitory Effect of the H1 Antagonist Loratadine on Histamine Release from Human Basophils," Int. Arch. Allergy Immunol., 1994, vol. 105, pp. 12-17.

Mirakhur, et al., "Glycopyrrolate: Pharmacology and Clinical Use," Anaesthesia, 1983, vol. 38, pp. 1195-1203.

Mitchelson, "Pharmacological Agents Affecting Emesis: A Review (Part II)," Drugs, 1992, vol. 43, No. 4, pp. 443-463.

Muskat, et al., "The Use of Scopolamine in the Treatment of Detrusor Instability," The J. of Urology, 1996, vol. 156, pp. 1989-1990.

Nelemans, "Antiallergic and antitussive drugs," Side Effects of Drugs Annual 12, Elsevier Science Publishers B.V., 1988, pp. 144-147.

Nomeir, et al., "Influence of Food on the Oral Bioavailability of Loratadine and Pseudoephedrine from Extended-Release Tablets in Healthy Volunteers," J. Clin. Pharm, 1996, vol. 36, No. 10, pp. 923-930.

Padhi, et al., Multiple-Dose Pharmaceokinetics; Safety and Tolerance of Desloratadine in Healthy Volunteers (Abstract 1124), Jan. 2000, J. Allergy Clin. Immunol., Jan. 2000, vol. 105, No. 1 part 2, p. S385.

Parkinson, et al., "Evaluation of Loratadine as an Inducer of Liver Microsomal Cytochrome P450 in Rats and Mice," Biochemical Pharmacology, 1992, vol. 43, No. 10, pp. 2169-2180.

Peggs, et al., "Antihistamines: The Old and the New," American Family Physician, Aug. 1995, vol. 52, No. 2, pp. 593-600.

Petrin, "Bewegungskrankheit and ihre Therapie/Eine Ubersicht (Motion Sickness and its Treatment)," Schweiz, Rundschau Med., 1974, (PRAXIS) 63, pp. 79-81.

Quercia, et al., "Focus on Loratadine: A new second-generation nonsedating H1-receptor antagonist," Hosp. Formul., Feb. 1993, vol. 28, pp. 137, 138, 141, 142, 144, 149 and 153.

Remington's Pharmaceutical Sciences, 18th Ed., Alfonso R. Gennaro, Mack Publishing Company, Easton, PA, 1990, pp. 1519-1520.

Remington's Pharmaceutical Sciences, 18th Ed., Alfonso R. Gennaro, Mack Publishing Company, Easton, PA, 1990, pp. 1527-1529.

Resnick, "Urinary incontinence," The Lancet, Jul. 8, 1995, vol. 346, pp. 94-99.

Roman, et al., "Loratadine—A Review of Recent Finding in Pharmacology Pharmacokinetics, Efficacy, and Safety, with a Look at its Use in Combination with Pseudoephedrine," Clin. Reviews in Allergy, 1993, vol. 11, pp. 89-110.

Salmun, et al., Efficacy and Safety of Desloratadine in Seasonal Allergic Rhinitis, Jan. 2000, J. Allergy Clin. Immunol. (Abstract 1123), vol. 105, No. 1, Part 2, pp. S384-S385.

Simons, "H1-Receptor Antagonists Comparative Tolerability and Safety," Drug Safety, 1994, vol. 10, No. 5, pp. 350-380.

Sunahara, et al., "Pharmacological interventions for motion sickness: Cardiovascular Effects," Aviation, Space and Environmental Medicine, Sep. 1987, pp. A270-A276.

Temple, et al., "Loratadine, an Antihistamine, Blocks Antigen- and Ionophore-Induced Leukotriene Release from Human Lung In Vitro," Prostaglandins, Apr. 1988, 35(4):549-554.

Van Cauwenberge, "New Data on the Safety of Loratadine," Drug Invest., 1992, vol. 4, No. 4, pp. 283-291.

Van Peer, et al., "Ketoconazole Inhibits Loratadine Metabolism in Man," Beerse, Belgium, (Abstract 1234), 1989, p. 34.

Wade, et al., Handbook of Pharmaceutical Excipients (2nd edition), American Pharmaceutical Association and Pharma Press, Royal Pharma, Society of G. Britain, 1994, pp. 257 and 259.

Wein, Pharmacology of Incontinence, Urologic Clinics of North America, Aug. 1995, vol. 22, No. 3, pp. 557-577.

Wirth, et al., Maillard Reaction of Lactose and Fluoxeline Hydrochloride, A Secondary Amine, Journal of Pharmaceutical Sciences, Jan. 1998, vol. 87, No. 1, pp. 31-39.

Wood, "Antimotion Sickness and Antiemetic Drugs," Drugs, 1979, vol. 17, pp. 471-479.

Wood, et al., "Mechanisms of Antimotion Sickness Drugs," Aviation, Space, and Environmental Medicine, Sep. 1987, pp. A262-A265.

The United States Pharmacopeia, The United States Formulary, United States Pharmacopeial Convention, Inc., Rockville, MD, 1989, p. 1990.

Yarker, et al., "Oxybutynin, A Review of its Pharmacodynamic and Phamacokinic Properties, and its Therapeutic Use in Detrusor Instability," Drugs and Aging, 1995, vol. 6, No. 3, pp. 243-262.

Zhong, et al., "HPLC-Determination of Loratadine and its active metabolite descarboethoxyloratadine in human plasma," Pharmazie, 1994, vol. 49(H. 10), pp. 736-739.

EXTENDED RELEASE ORAL DOSAGE COMPOSITION

CROSS REFERENCE TO RELATED APPLICATIONS

This application is a divisional application of U.S. application Ser. No. 10/699,987, filed Nov. 3, 2003, which is a continuation application of U.S. application Ser. No. 10/175,480 filed Jun. 19, 2002, now granted as U.S. Pat. No. 6,709,676 on Mar. 23, 2004, which is a continuation-in-part of International Application No. PCT/US00/34404 filed Dec. 19, 2000, from which priority is claimed pursuant to 35 U.S.C. §365(c) and §120, which application claims the benefit of U.S. Provisional Application Ser. No. 60/172,752 filed Dec. 20, 1999 under 35 U.S.C. §119(e).

BACKGROUND OF THE INVENTION

This invention relates to oral dosage compositions, including a bilayer sustained release oral dosage composition containing a nasal decongestant, e.g., pseudoephedrine in one layer and the non-sedating antihistamine, desloratadine in a second layer and having less than about 2% of desloratadine degradation products in the compositions. The oral dosage compositions of this invention are useful for treating patients showing the signs and symptoms associated with allergic and/or inflammatory conditions such as the common cold, as well as signs and symptoms associated with allergic and/or inflammatory conditions of the skin such as dermatitis, and airway passages such as the upper respiratory disease conditions, perennial allergic rhinitis, seasonal allergic rhinitis and nasal congestion, allergic asthma, and nasal congestion.

Desloratadine, also called descarbethoxyloratadine, is disclosed in U.S. Pat. No. 4,659,716 as a non-sedating antihistamine useful as an anti-allergy agent. U.S. Pat. No. 5,595,997 discloses methods and compositions for treating seasonal allergic rhinitis symptoms using desloratadine.

U.S. Pat. Nos. 4,990,535 and 5,100,675 disclose a twice-a-day sustained release coated tablet wherein the tablet coating comprises descarbethoxyloratadine and a hydrophilic polymer and polyethylene glycol, and the tablet core comprises acetaminophen, pseudoephedrine or a salt thereof, a swellable hydrophilic polymer and pharmaceutically acceptable excipients.

U.S. Pat. No. 5,314,697 discloses an extended release tablet containing matrix core comprising pseudoephedrine sulfate and a coating comprising loratadine.

None of the prior art discloses the solid oral dosage compositions of this invention.

The successful development of a formulation of a desloratadine-pseudoephedrine twice-a-day and once-a-day products would be desirable, but would require (1) achieving a release rate profile for pseudoephedrine component over an extended period of about twelve hours or twenty four hours, respectively, while maintaining the safety and effectiveness of desloratadine, and (2) minimizing impurity formation due to the interaction between desloratadine and excipients in the pseudoephedrine layer that are incompatible with desloratadine.

It would be desirable for increased patient compliance to have a stable, extended release desloratadine-pseudoephedrine product substantially free of desloratadine impurities and additional polymorphic forms that is effective and safe when used on a twice-a-day or once-a-day basis for the treatment, management and/or mitigation of the signs and symptoms associated with the common cold, as well as allergic and/or inflammatory conditions of the skin or upper and lower airway passages such as seasonal and perennial allergic rhinitis and nasal congestion.

SUMMARY OF THE INVENTION

We have found that desloratadine discolors and decomposes in the presence of excipients disclosed in the prior art. We have discovered that these problems are substantially solved by (a) bilayer solid compositions of the present invention wherein immediate release layer contains desloratadine combined with a pharmaceutically acceptable carrier medium comprising a desloratadine protective amount of a pharmaceutically acceptable basic salt, and wherein the use of an acidic excipient in the immediate release layer is substantially avoided or (b) bilayer solid compositions of the present invention wherein a desloratadine-protective amount of at least one pharmaceutically acceptable antioxidant is present in at least one layer, and preferably, wherein two of said antioxidants are present in desloratadine-containing immediate release layer.

Thus, this invention provides a bilayer solid composition comprising (a) an immediate release first layer comprising an anti-allergic effective amount of desloratadine and at least one pharmaceutically acceptable excipient and (b) a sustained release second layer comprising an effective amount of a nasal decongestant and a pharmaceutically acceptable sustained release agent wherein the total amount of desloratadine decomposition products in the composition is less than, or equal to, about 2% by weight.

This invention also provides a bilayer solid composition comprising (1) an immediate release first layer comprising an anti-allergic effective amount of desloratadine and a desloratadine-protective amount of a pharmaceutically acceptable water insoluble basic calcium, magnesium or aluminum salt, or of a desloratadine-protective amount of at least one pharmaceutically acceptable antioxidant; and (2) a sustained release second layer comprising an effective amount of pseudoephedrine or a salt thereof, and a pharmaceutically acceptable sustained release agent, and optionally a desloratadine-protective amount of a pharmaceutically acceptable antioxidant.

Thus, in one preferred embodiment, this invention provides a bilayer solid composition comprising (1) an immediate release first layer comprising an anti-allergic effective amount of desloratadine and desloratadine-protective amount of a pharmaceutically acceptable water insoluble basic calcium, magnesium or aluminum salt, and (2) a sustained release second layer comprising an effective amount of pseudoephedrine or a pharmaceutically acceptable salt thereof, and a pharmaceutically acceptable sustained release agent. The immediate release layer is substantially free of, i.e., contains less than about 1%, preferably, less than about 0.5%, and more preferably less than about 0.25% of acidic excipients.

The total amount of desloratadine decomposition products in the pharmaceutical compositions of this invention is less than, or equal to, about 2.0%, and preferably is less than, or equal to, about 1.4% by weight when such compositions are stored at 25° C. and about 60% relative humidity for extended time periods, e.g., at least about 12 to about 18 months.

In another preferred embodiment, this invention provides a bilayer solid composition comprising:
(a) an immediate release first layer comprising:

| INGREDIENT | mg/composition |
|---|---|
| Desloratadine, micronized | 2.5 |
| Corn starch | 11.0 |
| Dibasic calcium phosphate dihydrate | 53.0 |
| Microcrystalline cellulose | 30.22 |
| Talc | 3.0 |
| FD&C Blue dye No. 2 Aluminium Lake 5627 | 0.28 |
| TOTAL IN FIRST LAYER | 100.00 | and
(b) a second sustained release second layer comprising:

| INGREDIENT | mg/composition |
|---|---|
| Pseudoephedrine Sulfate | 120.0 |
| Hydroxypropyl Methylcellulose | 105.0 |
| Microcrystalline cellulose | 100.0 |
| Povidone | 18.0 |
| Silicon Dioxide | 5.0 |
| Magnesium stearate | 2.0 |
| TOTAL IN SECOND LAYER | 350.0 |

The total amount of desloratadine decomposition products such as N-formyl-desloratadine (see Chart I) in the above-listed preferred bilayer compositions is less than about 2.0% by weight when such compositions are stored at 25° C. and about 60% relative humidity for extended time periods of at least about 15 to about 18 months.

In another preferred embodiment, the present invention also provides a bilayer solid composition comprising (1) an immediate release first layer comprising an anti-allergic effective amount of desloratadine and a desloratadine-protective amount of at least one pharmaceutically acceptable antioxidant; and (2) a sustained release second layer comprising an effective amount of pseudoephedrine or a pharmaceutically acceptable salt thereof, a pharmaceutically acceptable sustained release agent, and a desloratadine-protective amount of a pharmaceutically acceptable antioxidant. The total amount of desloratadine decomposition products such as N-formyldesloratadine (see Chart I) in the above-listed preferred bilayer compositions is less than about 2.0% by weight when such compositions are stored at 25° C. and about 60% relative humidity for extended time periods of at least about 15 to about 18 months.

This invention further provides in another preferred embodiment a bilayer solid composition comprising (a) an immediate release first layer comprising an anti-allergic effective amount of desloratadine and at least one pharmaceutically acceptable excipient and (b) a sustained release second layer comprising an effective amount of pseudoephedrine or a pharmaceutically acceptable salt thereof and a pharmaceutically acceptable sustained release agent and wherein the total amount of desloratadine decomposition products in the bilayer solid composition is less than about 2.0% by weight when such compositions are stored at 25° C. and about 60% relative humidity for extended time periods of at least about 15 to about 18 months.

In another preferred embodiment, the present invention also provides a bilayer solid composition comprising (1) an immediate release first layer comprising 5 mg of desloratadine and desloratadine-protective amount of a pharmaceutically acceptable water insoluble basic calcium, magnesium or aluminum salt, and (2) a sustained release second layer comprising 120 mg of pseudoephedrine sulfate, and a pharmaceutically acceptable sustained release agent.

In another preferred embodiment, the present invention also provides a bilayer solid composition comprising (1) a first layer comprising 2.5 mg of desloratadine and a desloratadine-protective amount of at least one pharmaceutically acceptable antioxidant; and (2) a second layer comprising 120 mg of pseudoephedrine or a pharmaceutically acceptable salt thereof, a pharmaceutically acceptable excipient. Preferably there are two pharmaceutically acceptable antioxidants in the first immediate layer.

In another preferred embodiment, the present invention also provides a bilayer solid composition comprising (1) a first layer comprising 5.0 mg of desloratadine and a desloratadine-protective amount of at least one pharmaceutically acceptable antioxidant; and (2) a second layer comprising 120 mg of pseudoephedrine or a pharmaceutically acceptable salt thereof, a pharmaceutically acceptable excipient. Preferably there are two pharmaceutically acceptable antioxidants in the first immediate layer.

In another preferred embodiment, the present invention also provides a solid composition comprising 2.5 mg of desloratadine and a desloratadine-protective amount of at least one pharmaceutically acceptable antioxidant. Preferably, there are two pharmaceutically acceptable antioxidants in the solid compositions.

In another preferred embodiment, the present invention also provides a solid composition comprising 2.5 mg of desloratadine and a desloratadine-protective amount of at least one pharmaceutically acceptable antioxidant. Preferably, there are two pharmaceutically acceptable antioxidants in the solid composition.

We have also found that the total amount of desloratadine decomposition products in the 2.5 mg and 5.0 mg solid compositions is less than about 2.0%, and at least about 80% of the desloratadine in the 2.5 mg and 5.0 mg solid compositions of the present invention dissolves in 0.1N HCl at 37° C. in about 45 minutes.

Thus, the present invention also provides a method of using the solid compositions of the present invention for treating and/or preventing allergic and inflammatory conditions of the upper and lower airway passages and skin which comprises administering to a patient in need of such treating an effective amount of a solid composition of the present invention.

DETAILED DESCRIPTION OF THE INVENTION

During the course of development of the compositions of the present invention, desloratadine was found to be unstable and to discolor when stored in combination with various excipients such as those disclosed in U.S. Pat. No. 5,314,697 as part of the matrix core containing pseudoephedrine sulfate. We have discovered two solutions to minimize formation of desloratadine degradation products. In one embodiment, we incorporate a desloratadine protective amount of a pharmaceutically acceptable basic salt in the immediate release layer containing desloratadine, and substantially avoid the use of an acidic excipient in the immediate release layer. In the second embodiment, we incorporate a desloratadine-protective amount of at least one pharmaceutically acceptable antioxidant in at least one layer and preferably we incorporate two of said antioxidants into desloratadine-containing immediate release layer.

In the bilayer solid compositions containing a pharmaceutically acceptable water insoluble basic calcium, magnesium or aluminum salt, we found that the excipients in the immediate release layer causing discoloration and instability of desloratadine include acidic excipients having a pH of less than 7 in water such as organic acids, such as stearic acid, povidone, crospovidone as well as the hydroxycarboxylic acid, ascorbic acid, and carbonyl-containing materials such as lactose, and ethylcellulose and hydroxylpropyl methylcellulose. In this preferred embodiment, we also discovered that it is possible to prepare a bilayer tablet containing desloratadine in an immediate release first layer in intimate contact with a sustained release second layer containing a nasal decongestant and excipients incompatible with desloratadine by incorporating a desloratadine protective amount of a pharmaceutically acceptable water insoluble basic calcium, magnesium or aluminum salt into the immediate release desloratadine layer, and substantially avoiding the use of, that is having less than about 0.1% by weight, prefabably less than about 0.5%, and more prefabably less than about 0.25% of acidic excipients in the immediate release layer.

Binders like povidone and polymers such as hydroxypropyl methylcellulose are useful as a polymer matrix for the sustained release of a pharmaceutically acceptable pseudoephedrine salt, preferably pseudoephedrine sulfate, from the sustained release layer.

We also discovered that metal ions catalyzed were involved in the formation of desloratadine degradation products. In a preferred embodiment, a desloratadine-protective amount of a pharmaceutically acceptable anti-oxidant should be present in at least one of the bilayers, preferably one of said antioxidant is present in each layer, and more preferably two pharmaceutically acceptable anti-oxidants are present in the desloratadine layer.

The term "pharmaceutically acceptable antioxidant" as used herein in reference to desloratadine ("DL", formula I in the Chart) means a pharmaceutically acceptable chelating agent that protects desloratadine from the formation of degradation products including, but not limited to those of the formulas II-VII listed in the Chart, e.g., N-formyl-desloratadine or N-formyl DL (formula II in the Chart), N-hydroxylamine of DL (formula V in the Chart) N-oxide of DL (formula IV in the Chart), and the 3'-hydroxyl N-oxide of DL (formula III in the Chart), N-methyl DL (formula VI in the Chart), and the ketone of formula VII. The structures listed in the Chart were determined by standard physiochemical techniques, e.g., LC-MS, and LC-NMR.

Typically suitable pharmaceutically acceptable antioxidants for DL are pharmaceutically acceptable chelating agents such as those disclosed in "Chelating Agents", pages 764-794, Vol. 5 of KIRTH-OTHMER, ENCYCLOPEDIA OF CHEMICAL TECHNOLOGY, 4$^{th}$ Edition, 1993, John Wiley & Sons Inc., NY, and preferably including, but not limited to, hydroxycarboxylic acids, such as tartaric acid, citric acid and gluconic acid, and pharmaceutically acceptable salts thereof, aminocarboxylic acids such as iminodiacetic acid, N-methyliminodiacetic acid, nitrolotriacetic acid, edetic acid (ethylenediamine tetraacetic acid), diethylenetriaminepentaacetic acid, 1,2-diaminocyclohexanetetraacetic acid or N-hydroxylethylenediaminetriacetic acid, and pharmaceutically acceptable salts thereof such as the alkali and alkaline earth salts, e.g., edetate calcium disodium, edetate disodium, edetate trisodium, and edetate tetrasodium. Edetate disodium and citric acid are the preferred pharmaceutically acceptable antioxidants. Use of the hydroxycarboxylic acid, ascorbic acid, is to be avoided The desloratadine protective amount of a pharmaceutically acceptable antioxidant in the desloratadine immediate release layer is in the range of about 0.1% to about 10% by weight, preferably about 1% to 8% or about 1% to about 6%, more preferably about 3% to about 8%, or about 4% to about 6%, or most preferably about 5%. In a preferred embodiment of this invention, two antioxidants are present in the immediate release desloratadine layer, one antioxidant, e.g., edeate disodium, in an amount of about 1% to about 8%, preferably about 3% to about 8%, more preferably about 4% to about 6%, or most preferably about 5%, and the second antioxidant, e.g., citric acid, is present in an amount of about 1% to about 8%, preferably about 3% to about 8%, more preferably about 4% to about 6%, or most preferably about 5%. The pharmaceutically acceptable antioxidant in the pseudoephedrine sulfate ("PES") sustained release layer is in the range of 0% to about 10%, preferably about 0.1% to about 10%, or about 0.1% to about 3%, more preferably about 1 to about 2%, and most more preferably about 1.0%. In a preferred embodiment of the present invention, about 1.0% by weight of a pharmaceutically acceptable antioxidant, e.g., edetate disodium, is present in the PES sustained release layer. In another preferred embodiment, about 6% by weight of a mixture of two pharmaceutically acceptable antioxidants, e.g., edetate disodium and citric acid, are present in the DL immediate release layer in a ratio of about 5:1 to about 1:5, preferably about 5:1, and about 1% of a pharmaceutically acceptable antioxidant, e.g., edetate disodium, is present in the sustained release layer. In another preferred embodiment, about 5% by weight of one pharmaceutically acceptable antioxidant, e.g., edetate disodium, is present in the desloratadine immediate release layer.

In other preferred embodiments, about 5.0 mg of desloratadine is present in the immediate release layer, and 120 mg of the nasal decongestant, pseudoephedrine sulfate, is present in the sustained release layer (see Examples 4, 5 & 6). In one preferred embodiment, the dibasic phosphate salt preferably dibasic calcium phosphate dihydrate is present in the desloratadine immediate release layer and no pharmaceutically acceptable antioxidant is present in either layer (see Example 4). In another preferred embodiment, 5.0 mg of desloratadine and about 0.1 to about 10% of at least one antioxidant is present in the desloratadine immediate release layer, preferably about 4% to about 6% of a mixture of two antioxidants, e.g., edetate disodium and citric acid, in a ratio of 5:1 to 1:1, preferably in a ratio of 5:1, and about 0.1% to about 10% preferably about 0.1% to about 5%, more preferably about 0.1% to about 3%, most more preferably about 1.0% of an antioxidant, e.g., edetate disodium, is present in the PES sustained release layer (see Examples 5&6).

The desloratadine was found to have an acceptable immediate release profile from the immediate release layer (80% release in 0.1N HCl in less than about 45 min.) and contain less than about 2% of desloratadine degradation products even after storage for at least 18 months at 25° C. and about 60% relative humidity ("RH").

In another preferred embodiment, the present invention also provides a solid composition comprising 2.5 mg of desloratadine and a desloratadine-protective amount of at least one pharmaceutically acceptable antioxidant. Preferably, there are two pharmaceutically acceptable antioxidants in the solid compositions. See Example 9. In another preferred embodiment, the present invention also provides a solid composition comprising 5.0 mg of desloratadine and a desloratadine-protective amount of at least one pharmaceutically acceptable antioxidant. Preferably, there are two pharmaceutically acceptable antioxidants in the solid composition. See for example, Example 10. The desloratadine protective amount of a pharmaceutically acceptable antioxidant in the 5.0 mg and 2.5 mg solid compositions is in the range of about 0.1% to about 10% by weight, preferably about 1% to 8% or about 1% to about 6%, more preferably about 3% to about 8%, or about 4% to about 6%, or most preferably about 5%. In a preferred embodiment of this invention, two antioxidants are present in the 5.0 mg and 2.5 mg solid compositions; one antioxidant, e.g., edeate disodium, in an amount of about 1% to about 8%, preferably about 3% to about 8%, more preferably about 4% to about 6%, or most preferably about 5%, and the second antioxidant, e.g., citric acid, is present in an amount of about 1% to about 8%, preferably about 3% to about 8%, more preferably about 4% to about 6%, or most preferably about 5%. In another preferred embodiment, about 6% by weight of a mixture of two pharmaceutically acceptable antioxidants, e.g., edetate disodium and citric acid, are present in the 5.0 mg and 2.5 mg solid compositions in a ratio of about 5:1 to about 1:5, preferably about 1:1. It has been surprisingly found that stearic acid could be used in place of talc to overcome a tooling problem in the 5.0 mg and 2.5 mg solid compositions containing two pharmaceutically acceptable antioxidants, e.g., edetate disodium and citric acid, without adversely affecting the total amount of desloratadine decomposition products.

We have found that the total amount of desloratadine decomposition products in the 5.0 mg and 2.5 mg solid compositions containing two pharmaceutically acceptable antioxidants, e.g., edetate disodium and citric acid, is less than about 2.0%, and preferably about 1.5% by weight or less after storage at 25 c and 60% RH for extended time periods of at least 12 up to 15 months. In addition, at least about 80% of the desloratadine in the 5.0 mg and 2.5 mg solid compositions containing two pharmaceutically acceptable antioxidants, e.g., edetate disodium and citric acid, dissolves in 0.1N HCl at 37° C. in about 45 minutes.

In another preferred embodiment, a desloratadine-protective amount of a pharmaceutically acceptable anti-oxidant should be present in at least one of the bilayers, preferably one of said antioxidant in each layer.

The two layers of the bilayer tablets of this invention may be in intimate contact with one another, or have a layer at the interfaces of the two layers. The layer at the interfaces of the two layers may be a water-swellable film-forming polymer containing one or more pharmaceutically acceptable excipients or the layer may also contain at least one pharmaceutically acceptable antioxidant.

The term "in intimate contact" as used herein in reference to the two layers forming the bilayer tablet means that there is with no film interface between the two layers.

The term "water-swellable film-forming neutral or cationic copolymeric ester," as used herein means neutral and cationic copolymers of ethyl acrylate and substituted unsubstituted methyl or ethyl methacrylate esters.

Typically suitable water swellable film-forming neutral copolymeric esters include neutral copolymers of ethyl acrylate and methyl metharylate such as are available from Pharma Poloymers, a company of the Hüls Group under the EUDRAGIT® Tradename; EUDRAGIT NE30D. and Kollicoat available from BASF, Mt Olive, N.J. An aqueous dispersion containing 30% by weight of a neutral copolymer based on ethyl crylate and methyl methoacrylate (average molecular weight of approximately 800,000) is preferred.

Typically suitable water-swellable film-forming cationic co-polymeric esters include cationic co-polymerers based on dimethylaminoethylmethacrylate and a neutral methacrylic ester such as the EUDRAGIT E copolymers available from Pharma Polymers as a 12.5% solution (EUDRAGIT E 12.5) or as solid (EUDRAGIT E 100) and quaternay ammonium copolymers described in USP/NF as "Amononio methacrylate copolymer, Type A" and Type "B". Such copolymers are available as aqueous dispersions of copolymers of acrylic and methacrylic acid esters with a low (substitution) content of quaternary ammonium groups present as salts, (e.g., quaternary ammonium chlorides). Type A and Type B are available as 30% aqueous dispersions under the EUDRAGIT RL 30D and EUDRAGIT RS 30D tradenames, respectively. Use of the water-swellable film—from neutral co-polymeric esters based on ethyl acrylate and methacrylate is preferred.

The term "water soluble film modifier" as used herein means a film-forming agent which modifies the water-swellable characteristics of the film-forming neutral or cationic copolymeric esters useful in the layer at the interface of the bilayer compositions of the present invention. A typically suitable water soluble film-modifying agent is a low viscosity ($\leqq 20$ cps) cellulose such as low viscosity hydroxypropyl methyl cellulose, low viscosity hydroxyethyl methyl cellulose; low viscosity sodium carboxymethyl cellulose or a polyethylene glycol selected from polyethylene glycol 200 to polyethylene glycol 8000.

Use of a polyethylene glycol 6000 to polyethylene glycol 8000 as a film modifier is preferred.

The phrase "allergic and inflammatory conditions of the skin and airway passages" means those allergic and inflammatory conditions and symptoms found on the skin and in the upper and lower airway passages from the nose to the lungs. Typical allergic and inflammatory conditions of the skin and upper and lower airway passages include seasonal and perennial allergic rhinitis, non-allergic rhinitis, asthma including allergic and non-allergic asthma, sinusitis, colds (in combination with a NSAID, e.g., aspirin ibuprofen or APAP) and/or a decongestant e.g. pseudoephedrine), dermatitis, especially allergic and atopic dermatitis, and urticaria and symptomatic dermographism as well as retinophathy, and small vessel diseases, associated with diabetes mellitus.

The amount of desloratadine effective for treating or preventing allergic and inflammatory conditions of the skin and upper and lower airway passages will vary with the age, sex, body weight and severity of the allergic and inflammatory condition of the patient. Typically, the amount of desloratadine effective for treating or preventing such allergic and inflammatory conditions is in the range of about 2.5 mg/day to about 60 mg/day, preferably about 2.5 mg/day to about 20 mg/day, or about 4.0 mg/day to about 15 mg/day, or about 5.0 mg/day to about 10 mg/day, more preferably about 5.0 mg/day to about 10.0 mg/day, and most preferably about 5.0 mg/day in one dose or in two divided doses of 2.5 mg/dose.

Desloratadine is a non-sedating long acting histamine antagonist with potent selective peripheral H1-receptor antagonist activity. Following oral administration, loratadine is rapidly metabolized to descarboethoxyloratadie or desloratadine, a pharmacologically active metabolite. In vitro and in vivo animal pharmacology studies have been conducted to assess various pharmacodynamic effects of desloratadine and loratadine. In assessing antihistamine activity in mice (comparison of $ED_{50}$ value), desloratadine was relatively free of producing alterations in behavior alterations in behavior, neurologic or autonomic function. The potential for desloratadine or loratadine to occupy brain H1-receptors was assessed in guinea pigs following i.p. administration and results suggest poor access to central histamine receptors for desloratadine or loratadine.

In addition to antihistaminic activity, desloratadine has demonstrated anti-allergic and anti-inflammatory activity from numerous in vitro and in vivo tests. These in vitro tests (mainly conducted on cells of human origin) have shown that desloratadine can inhibit many events in the cascade of allergic inflammation. These anti-inflammatory effects for desloratadine are independent of the H1-antagonist effect of desloratadine and include:

The release of inflammatory mediators histamine, truptase, leukotriene and prostaglandin D2 from mast cells;

The release of inflammatory cytokines including IL-4, IL-6, IL-8 and IL-13;

The release of the inflammatory chemokines such as RANTES (regulated upon activation, normal T cell expressed and presumably secreted);

Superoxide anion production of polymorphonuclear-neutrophils;

The expression of cell adhesion molecules such as intracellular adhesion molecules (ICAM-1) and P-selection in endothelial cells; and Eosinophil migration and adhesion In vivo studies also suggest that an inhibitory effect of desloratadine on allergic bronchospasm and cough can also be expected.

The clinical efficacy and safety of desloratadine has been documented in over 3,200 seasonal allergic rhinitis patients in 4 double-blind, randomized clinical trials. The results of these chemical studies demonstrated the efficacy of desloratadine in the treatment of adult and adolescent patients with seasonal rhinitis.

The nasal decongestants useful in the present invention include phenylpropanolamine, phenylephrine and pseudoephedrine. Pseudoephedrine as well as pharmaceutically acceptable acid additional salts, e.g., those of HCl or $H_2SO_4$, is a sympathomimetic drug recognized by those skilled in the art as a safe therapeutic agent effective for treating nasal congestion and is commonly administered orally and concomitantly with an antihistamine for treatment of nasal congestion associated with allergic rhinitis. The use of pseudoephedrine as a nasal decongestant in the present invention is preferred; the use of about 120 mg pseudoephedrine sulfate in the extended release layer is more preferred. However, lesser amounts of pseudoephedrine sulfate may be used in combination with desloratadine, e.g., in combination with the 2.5 and 5.0 solid compositions of the present invention such as described in Examples 9 and 10.

In the course of development of the compressed bilayer oral dosage composition of this invention, it was discovered that the selection of the polymers for the extended release layer was critical to achieve the desired extended release period of at least 12 hours, for pseudoephedrine sulfate. For example, the use of hydroxypropyl methylcellulose 4,000 cps or 15,000 cps as polymers in the matrix core did not provide this more preferred extended release period of at least 16 hours for dose of pseudoephedrine sulfate. We discovered that only by selecting for inclusion into the matrix core of specific weight ratios of three specific polymers was the desired pseudoephedrine release profile achieved. Only by combining (1) about one part by weight, preferably 1.05 parts by weight of hydroxypropyl methylcellulose 2208 USP, 100,000 cps with (2) about one part by weight, preferably 1.0 parts by weight of microcrystalline cyellulose together with (3) about 0.15-0.20 part by weight, preferably 0.17-0.18 parts by weight of povidone (per 1.05 parts by weight of hydroxypropyl methylcellulose) as a secondary binder was the more preferred extended release profile of at least 12 hours for pseudoephedrine sulfate from the extended release layer. The extended release layer also contains specific amounts of silicon dioxide as a glidant and magnesium stearate as a lubricant. The tablet hardness 20±4 Strong-Cobb Units (SCU) is not greatly affected by the higher level of lubricant (6 mg/tablet) but it is preferred to maintain the lubricant level at ⅕ part by weight of lubricant to one part by weight of povidone as secondary binder.

The term "lubricant' as used herein refers to a substance added to the dosage form to enable the dosage form, e.g., a tablet, after it has been compressed to release from the mold or die.

Suitable lubricants include talc, magnesium stearate, calcium stearate, stearic acid, hydrogenated vegetable oils and the like. Preferably, magnesium stearate or talc is used.

The term "glidants" as used herein refers to a substance, such as an anti-caking agent, which improves the flow characteristics of a powder mixture.

Suitable glidants include silicon dioxide and talc. Preferably, silicon dioxide is used.

The term "binders" as used herein means any material that is added to pharmaceutical compositions to help hold such compositions together and release the medicament therefrom.

Suitable binders are selected those found in NF XVIII, page 2206 (1995) and include povidones, starches, celluloses, alginates, and gums and low molecular weight hydroxypropyl melthyl celluloses, especially hydroypropyl methyl celluose 2910.

The term "pharmaceutically acceptable water insoluble basic calcium, magnesium and aluminium salts" as used herein means the pharmaceutically acceptable carbonates, phosphates, silicates and sulfates of calcium, magnesium and aluminum or mixtures thereof. Typically suitable pharmaceutically acceptable basic salts include calcium sulfate anhydrous, hydrates of calcium sulfate, such as calcium sulfate dihydrate, magnesium sulfate anhydrous, hydrates of magnesium sulfate, dibasic calcium phosphate, dibasic calcium silicate, magnesium trisilicate, magnesium phosphate, aluminum silicate, and hydrates of magnesium phosphate, aluminum phosphate; and calcium phosphate is more preferred. The use of dibasic calcium phosphate dihydrate is most preferred.

The desloratadine-protective amount of a pharmaceutically acceptable water insoluble basic calcium, magnesium or aluminum salt is in the range of about 50-60% of the DL immediate release layer, and the w/w ratio of the pharmaceutically acceptable water insoluble basic calcium, magnesium or aluminum salt to DL is in the range of about 8:1 to about 40:1, more preferably is in the range of about 10:1 to about 20:1, and most preferably is in the range of about 10:1 to about 11:1.

In the preferred embodiment of the present invention wherein a desloratadine protective amount of a pharmaceutically acceptable antioxidant is present, the water insoluble basic calcium salt is not present in the immediate release layer containing desloratadine; in its place, at least one, preferably two pharmaceutically acceptable antioxidants are present, e.g., edetate sodium and citric acid and the amount of microcrystalline cellulose is increased. In addition, when the pharmaceutically acceptable antioxidant is used in place of the water insoluble basic calcium, magnesium or aluminum salt, the povidone in the sustained release layer is replaced by another binder, preferably a low molecular weight hydroxypropyl methyl cellulose ("HPMC"), preferably HPMC 2910.

In the preparation of the bilayer tablet, the sustained release layer is compacted first. The immediate release second layer is added on top and a compression force sufficient to form a bilayer tablet is applied in the range of 8-12 kilo Newtons, preferably about 9 kilo Newtons (kN).

The dried sustained release granulation is milled and blended with requisite amounts of silicon dioxide and magnesium stearate. In a preferred embodiment, a pharmaceutically acceptable blue dye containing EDTA as a chelating agent is incorporated into the immediate release desloratadine layer. Use of a pharmaceutically acceptable blue dye, e.g. FD& C blue dye No. 2 Aluminum Lake 5627 is preferred.

Example 1

This example illustrates preparation of the preferred oral dosage composition of this invention. The ingredients and specific amounts thereof are listed below.

A. Method of Manufacture of the Immediate Release Layer
1. Prepare starch paste by dispersing the paste portion of corn starch into purified water in a suitable container equipped with an agitator.
2. While mixing, heat the contents to approximately 95° C. and maintain the temperature for approximately 30 minutes.
3. After Step 2 is completed, add an additional purified water and allow the starch paste to cool to approximately 50° C.
4. While mixing, add desloratadine to the starch paste. Continue mixing during the granulation step.
5. Pass the FD&C blue No. 2 aluminum lake containing EDTA as a chelating, e.g., Spectra Spray Med Blue, with the required amount of dibasic calcium phosphate through a suitable sieve or mill.
6. Charge to a suitable fluid bed processing bowl the remaining dibasic calcium phosphate dihydrate, the milled material from Step 5, a portion of the corn starch, and a portion of microcrystalline cellulose. Place the processing bowl into the fluid bed processor.
7. Fluidize the powder bed until the product temperature reaches approximately 29° C.
8. Begin granulating the powder by pumping the starch paste from Step 4 into the fluidized bed at a suitable spray rate and a bed temperature of approximately 22° C.
9. Continue to dry the granulation at an inlet air temperature of approximately 60° C. until a final loss on drying (LOD) of 2% or less is achieved.
10. Pass the dried granulation through a suitable sieve or mill.
11. Charge the granulation to a suitable blender and add the requisite amounts of the remaining portion of microcrystalline cellulose, corn starch, and talc. Blend for 5 minutes.

B. Manufacture of Sustained Release Mix:
1. Charge purified water and alcohol to a suitable container equipped with an agitator.
2. Dissolve povidone in the water/alcohol mixture. Continue mixing for a minimum of 10 minutes.
3. Mix hydroxypropyl methylcellulose, pseudoephedrine sulfate and microcrystalline cellulose in a suitable granulator.
4. Granulate the mix with the povidone solution, using additional water/alcohol mixture if necessary to achieve the appropriate granulation consistency.
5. Dry the wet granulation at approximately 50° C. in a suitable dryer until the loss on drying (LOD) is between 1% and 3%.
6. Pass the dried granulation through a suitable sieve or mill.
7. Charge the milled granulation to a suitable blender.
8. Pass the silicon dioxide through a No. 30 mesh screen into the blender.
9. Blend the requisite amount of screened silicon dioxide with the granulation for approximately 10 minutes in a suitable blender.
10. Pass the magnesium stearate through a No. 30 mesh screen.
11. Blend the requisite amount of screened magnesium stearate with the mix from Step 9 for 5 minutes.

C. Compression:
Compress the two blends to specifications as bilayer tablets using a suitable double-layer tablet press using a compression force of 9 k Newtons. Compress the sustained release layer first.

Tablet Weight: 450 mg±5%
  Sustained release layer: 350 mg±5%
  Immediate release layer 100 mg±5%
Hardness: 20±4 SCU (Strong Cobb units)

The following bilayer tablet was prepared using the above procedure.

Desloratadine Immediate Release Layer:

| INGREDIENT | mg/composition |
| --- | --- |
| Desloratadine, micronized | 2.5 |
| Corn Starch NF/Ph. Eur. | 11.0 |
| Dibasic Calcium Phosphate Dihydrate USP/Ph. Eur. | 53.0 |
| Microcrystalline Cellulose NF/Ph. Eur./JP | 30.22 |
| Talc USP/Ph. Eur. | 3.0 |
| Dye FD&C Blue No. 2 Aluminium Lake 5627 | 0.28 |
| Water Purified USP/Ph. Eur. | — |
| TOTAL | 100.00 | and

Pseudoephedrine Sulfate Sustained Release Layer

| INGREDIENT | mg/composition |
| --- | --- |
| Pseudoephedrine Sulfate USP | 120.0 |
| Hydroxypropyl Methylcellulose 2208, USP, 100,000 cps (K100M)/Ph. Eur. | 105.0 |
| Microcrystalline Cellulose NF/Ph. Eur./JP | 100.0 |
| Povidone USP/Ph. Eur./JP | 18.0 |
| Silicon Dioxide NF | 5.0 |
| Magnesium Stearate NF/Ph. Eur. JP(Non-Bovine) | 2.0 |
| Water Purified USP/Ph. Eur. | — |
| Alcohol USP/3A Alcohol | — |
| TOTAL | 350.0 |
| TOTAL TABLET | 450.0 |

Hardness: 20±4 SCU (Strong Cobb units)

Example 2

The procedure of Example 1 was used; edetate disodium was used in place of the dibasic calcium salt and the amount of microcrystalline cellulose in the DL layer was increased. Edetate disodium was used in the sustained release layer and hydroxypropyl methylcellulose 2910 was used in place of povidone.

Desloratadine Immediate Release Layer:

| INGREDIENT | mg/composition |
| --- | --- |
| Desloratadine, micronized | 2.5 |
| Corn Starch NF/Ph. Eur. | 8.0 |
| Microcrystalline Cellulose NF/Ph. Eur./JP | 71.35 |
| Edetate Disodium | 5.0 |
| Talc USP/Ph. Eur. | 3.0 |
| Dye FD&C Blue No. 2 Aluminium Lake 5627 | 0.15 |
| Water Purified USP/Ph. Eur. | — |
| TOTAL | 100.00 | and
Pseudoephedrine Sulfate Sustained Release Layer

| INGREDIENT | mg/composition |
| --- | --- |
| Pseudoephedrine Sulfate USP | 120.0 |
| Hydroxypropyl Methylcellulose 2208, USP/Ph. Eur. | 105.0 |
| Microcrystalline Cellulose NF/Ph. Eur./JP | 103.5 |
| Edetate Disodium | 3.5 |
| Hydroxypropyl Methylcellulose 2910 USP/Ph. Eur./JP | 10.5 |
| Silicon Dioxide NF | 5.0 |
| Magnesium Stearate NF/Ph. Eur. JP(Non-Bovine) | 2.5 |
| Water Purified USP/Ph. Eur. | — |
| Alcohol USP/3A Alcohol | — |
| TOTAL | 350.0 |
| TOTAL TABLET | 450.0 |

Hardness: 20±4 SCU (Strong Cobb units)

Example 3

The procedure of Example 2 was used, but 1 mg of citric acid was added to the DL layer and the amount of microcrystalline cellulose was decreased by 1 mg.
Desloratadine Immediate Release Layer:

| INGREDIENT | mg/composition |
| --- | --- |
| Desloratadine, micronized | 2.5 |
| Corn Starch NF/Ph. Eur. | 18.0 |
| Edetate Disodium | 5.0 |
| Citric Acid | 1.0 |
| Microcrystalline Cellulose NF/Ph. Eur./JP | 70.35 |
| Talc USP/Ph. Eur. | 3.0 |
| Dye FD&C Blue No. 2 Aluminium Lake 5627 | 0.15 |
| Water Purified USP/Ph. Eur. | — |
| TOTAL | 100.00 |

And Pseudoephedrine Sulfate Sustained Release Layer

| INGREDIENT | mg/composition |
| --- | --- |
| Pseudoephedrine Sulfate USP | 120.0 |
| Hydroxypropyl Methylcellulose 2208, 100,000 cps (K100M)USP/Ph. Eur. | 105.0 |
| Microcrystalline Cellulose NF/Ph. Eur./JP | 103.5 |
| Edetate Disodium | 3.5 |
| Hydroxypropyl Methylcellulose 2910 | 10.5 |
| Silicon Dioxide NF | 5.0 |
| Magnesium Stearate NF/Ph. Eur. JP(Non-Bovine) | 2.5 |
| Water Purified USP/Ph. Eur. | — |
| Alcohol USP/3A Alcohol | — |
| TOTAL | 350.0 |
| TOTAL TABLET | 450.0 |

Hardness: 20±4 SCU (Strong Cobb units)

Example 4

The procedure of Example 1 was used. The bilayer tablet of Example 1 was modified by including 5.0 mg of desloratadine in the immediate release layer—(a 24 hour dose)—with the appropriate changes in amounts of the other ingredients and using the 12-hr dose pseudoephedrine sustained release layer of Example 1. Hardness: 20±4 SCU (Strong Cobb units)
Desloratadine Immediate Release Layer:

| INGREDIENT | mg/composition |
| --- | --- |
| Desloratadine, micronized | 5.0 |
| Corn Starch NF/Ph. Eur. | 11.0 |
| Dibasic Calcium Phosphate Dihydrate USP/Ph. Eur. | 53.0 |
| Microcrystalline Cellulose NF/Ph. Eur./JP | 27.72 |
| Talc USP/Ph. Eur. | 3.0 |
| Dye FD&C Blue No. 2 Aluminium Lake 5627 | 0.28 |
| Water Purified USP/Ph. Eur. | — |
| TOTAL | 100.00 | and
Pseudoephedrine Sulfate Sustained Release Layer

| INGREDIENT | mg/composition |
| --- | --- |
| Pseudoephedrine Sulfate USP | 120.0 |
| Hydroxypropyl Methylcellulose 2208, 1000,00 cps (K100M)USP/Ph. Eur. | 105.0 |
| Microcrystalline Cellulose NF/Ph. Eur./JP | 100.0 |
| Povidone USP/Ph. Eur./JP | 18.0 |
| Silicon Dioxide NF | 5.0 |
| Magnesium Stearate NF/Ph. Eur. JP(Non-Bovine) | 2.0 |
| Water Purified USP/Ph. Eur. | — |
| Alcohol USP/3A Alcohol | — |
| TOTAL | 350.0 |
| TOTAL TABLET | 450.0 |

Example 5

The procedure of Example 1 was used and the bilayer tablet of Example 4 was modified by replacing the dibasic calcium phosphate dihydrate in the immediate release layer with 10 mg of edetate disodium and increasing the amount of microcrystalline cellulose by 2.7 mg. Hardness: 20±4 SCU (Strong Cobb units)
Desloratadine Immediate Release Layer:

| INGREDIENT | mg/composition |
| --- | --- |
| Desloratadine, micronized | 5.0 |
| Corn Starch NF/Ph. Eur. | 36.0 |

-continued

| INGREDIENT | mg/composition |
|---|---|
| Microcrystalline Cellulose NF/Ph. Eur./JP | 142.7 |
| Edetate Disodium | 10.0 |
| Talc USP/Ph. Eur. | 6.0 |
| Dye FD&C Blue No. 2 Aluminium Lake 5627 | 0.30 |
| Water Purified USP/Ph. Eur. | — |
| TOTAL | 200.00 | and
Pseudoephedrine Sulfate Sustained Release Layer

| INGREDIENT | mg/composition |
|---|---|
| Pseudoephedrine Sulfate USP | 120.0 |
| Hydroxypropyl Methylcellulose 2208, 1000,00 cps USP/Ph. Eur. | 105.0 |
| Microcrystalline Cellulose NF/Ph. Eur./JP | 103.5 |
| Hydroxypropyl Methylcellulose 2910 | 10.5 |
| Edetate Disodium | 3.5 |
| Silicon Dioxide NF | 5.0 |
| Magnesium Stearate NF/Ph. Eur. JP(Non-Bovine) | 2.5 |
| Water Purified USP/Ph. Eur. | — |
| Alcohol USP/3A Alcohol | — |
| TOTAL | 350.0 |
| TOTAL Tablet Weight | 550.0 |

Example 6

The bilayer tablet of Example 5 was modified by adding 2.0 mg of citric acid to the immediate release layer and decreasing the amount of microcrystalline cellulose by 2.7 mg and using the pseudoephedrine sustained release layer of Example 1. Hardness: 20±4 SCU (Strong Cobb units)

Desloratadine Immediate Release Layer:

| INGREDIENT | mg/composition |
|---|---|
| Desloratadine, micronized | 5.0 |
| Corn Starch NF/Ph. Eur. | 36.0 |
| Microcrystalline Cellulose NF/Ph. Eur./JP | 140.7 |
| Edetate Disodium | 10.0 |
| Citric Acid | 2.0 |
| Talc USP/Ph. Eur. | 6.0 |
| Dye FD&C Blue No. 2 Aluminium Lake 5627 | 0.30 |
| Water Purified USP/Ph. Eur. | — |
| TOTAL | 200.00 |

And Pseudoephedrine Sulfate Sustained Release Layer

| INGREDIENT | mg/composition |
|---|---|
| Pseudoephedrine Sulfate USP | 120.0 |
| Hydroxypropyl Methylcellulose 2208, 1000,00 cps USP/Ph. Eur. | 105.0 |
| Microcrystalline Cellulose NF/Ph. Eur./JP | 103.5 |
| Hydroxypropyl Methylcellulose 2910 | 10.5 |
| Edetate Disodium | 3.5 |
| Silicon Dioxide NF | 5.0 |
| Magnesium Stearate NF/Ph. Eur. JP(Non-Bovine) | 2.5 |

-continued

| INGREDIENT | mg/composition |
|---|---|
| Water Purified USP/Ph. Eur. | — |
| Alcohol USP/3A Alcohol | — |
| TOTAL | 350.0 |
| TOTAL Tablet Weight | 550.0 |

Example 7

The bilayer tablet of Example 5 was modified by replacing the talc with an equivalent weight of stearic acid, and by adding an additional 8.0 mg of citric acid to the immediate release layer and decreasing the amount of microcrystalline cellulose by 8.0 mg and replacing 4.0 g of the microcrystalline cellulose and all of the hydroxypropyl methylcellulose and edetate disodium with 18.0 g of popovidone the pseudoephedrine in the sustained release layer of Example 6.

Desloratadine Immediate Release Layer:

| INGREDIENT | mg/composition |
|---|---|
| Desloratadine, micronized | 5.0 |
| Corn Starch NF/Ph. Eur. | 36.0 |
| Microcrystalline Cellulose NF/Ph. Eur./JP | 132.7 |
| Edetate Disodium USP | 10.0 |
| Citric Acid Anhydrous, USP | 10.0 |
| Stearic Acid, NF. | 6.0 |
| Dye FD&C Blue No. 2 Aluminium Lake 5627 | 0.30 |
| Water Purified USP/Ph. Eur. | — |
| TOTAL | 200.00 |

And Pseudoephedrine Sulfate Sustained Release Layer

| INGREDIENT | mg/composition |
|---|---|
| Pseudoephedrine Sulfate USP | 120.0 |
| Hydroxypropyl Methylcellulose 2208, 1000,00 cps USP/Ph. Eur(K100M). | 105.0 |
| Microcrystalline Cellulose NF/Ph. Eur./JP | 99.5 |
| Povidone, USP | 18.0 |
| Silicon Dioxide NF | 5.0 |
| Magnesium Stearate NF/Ph. Eur. JP(Non-Bovine) | 2.5 |
| Water Purified USP/Ph. Eur. | — |
| Alcohol USP/3A Alcohol | — |
| TOTAL | 350.0 |
| TOTAL Tablet Weight | 550.0 |

Example 8

The bilayer tablet of Example 7 was modified by decreasing the weight of all ingredients in the desloratadine immediate release layer by 50% and using the sustained release layer of Example 7

Desloratadine Immediate Release Layer:

| INGREDIENT | mg/composition |
|---|---|
| Desloratadine, micronized | 2.5 |
| Corn Starch NF/Ph. Eur. | 18.0 |
| Microcrystalline Cellulose NF/Ph. Eur./JP | 66.35 |
| Edetate Disodium USP | 5.0 |
| Citric Acid Anhydrous, USP | 5.0 |
| Stearic Acid, NF. | 3.0 |

-continued

| INGREDIENT | mg/composition |
|---|---|
| Dye FD&C Blue No. 2 Aluminium Lake 5627 | 0.15 |
| Water Purified USP/Ph. Eur. | — |
| TOTAL | 100.00 |

And Pseudoephedrine Sulfate Sustained Release Layer

| INGREDIENT | mg/composition |
|---|---|
| Pseudoephedrine Sulfate USP | 120.0 |
| Hydroxypropyl Methylcellulose 2208, 1000,00 cps USP/Ph. Eur(K100M). | 105.0 |
| Microcrystalline Cellulose NF/Ph. Eur./JP | 99.5 |
| Povidone, USP | 18.0 |
| Silicon Dioxide NF | 5.0 |
| Magnesium Stearate NF/Ph. Eur. JP(Non-Bovine) | 2.5 |
| Water Purified USP/Ph. Eur. | — |
| Alcohol USP/3A Alcohol | — |
| TOTAL | 350.0 |
| TOTAL Tablet Weight | 450.0 |

Example 9

A desloratadine (2.5 mg) tablet was prepared by using the desloratadine immediate release layer of Example 8.

| INGREDIENT | mg/composition |
|---|---|
| Desloratadine, micronized | 2.5 |
| Corn Starch NF/Ph. Eur. | 18.0 |
| Microcrystalline Cellulose NF/Ph. Eur./JP | 66.35 |
| Edetate Disodium USP | 5.0 |
| Citric Acid Anhydrous, USP | 5.0 |
| Stearic Acid, NF. | 3.0 |
| Dye FD&C Blue No. 2 Aluminium Lake 5627 | 0.15 |
| Water Purified USP/Ph. Eur. | — |
| TOTAL Tablet Weight | 100.00 |

Example 10

A desloratadine (5.0 mg) tablet was prepared by using the desloratadine immediate release layer of Example 7.

| INGREDIENT | mg/composition |
|---|---|
| Desloratadine, micronized | 5.0 |
| Corn Starch NF/Ph. Eur. | 36.0 |
| Microcrystalline Cellulose NF/Ph. Eur./JP | 132.7 |
| Edetate Disodium USP | 10.0 |
| Citric Acid Anhydrous, USP | 10.0 |
| Stearic Acid, NF. | 6.0 |
| Dye FD&C Blue No. 2 Aluminium Lake 5627 | 0.30 |
| Water Purified USP/Ph. Eur. | — |
| TOTAL TABLET WEIGHT | 200.00 |

The in vitro dissolution profile of the tablets of Examples 1-10 were measured in a stirred 0.1N HCl solution at 37° C. ($1^{st}$ hour) and thereafter in a stirred phosphate buffer having a pH of 7.5 at 37° C. The 80% of desloratadine in the immediate release layers was dissolved within the first 30 minutes and the total dose of pseudoephedrine sulfate in the sustained release layers of Examples 1-8 was slowly released via erosion and dissolution mechanisms over a period of at least 12 hours. (with 30-45% in 1 hr, 50-605% in 2 hrs. and $\geq 80\%$ in 6 hrs).

Similar results would be expected if a decongestant effective amount of another pharmaceutically acceptable pseudoephedrine salt, e.g., pseudoephedrine hydrochloride was used in place of pseudoephedrine sulfate.

The compositions of the present invention are useful for treatment of allergic and/or inflammatory conditions of the skin (e.g. urticaria) and the upper and lower airway passages including the nasal and non-nasal symptoms of perennial and seasonal allergic rhinitis including nasal congestion in a patient in need of such treating. The precise dosage and dosage regimen may be varied by the attending clinician in view of the teachings herein depending upon the requirements of the patient, e.g., the patients age, sex and the severity of the allergic and/or inflammatory condition being treated. Determination of the proper dosage and dosage regimen for a particular patient will be within the skill of the attending clinician. While we have hereinabove presented a number of preferred embodiments of this invention by way of example, it is apparent that the scope of the invention is to be defined by the scope of the appended claims.

CHART

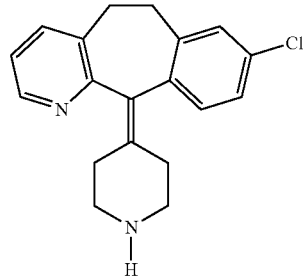

I

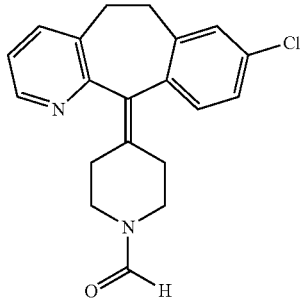

II

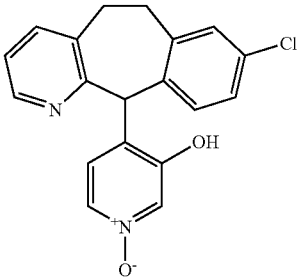

III

-continued

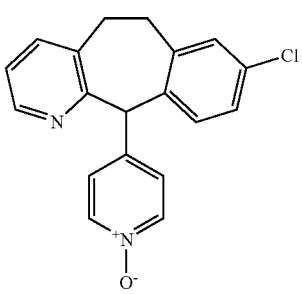
IV

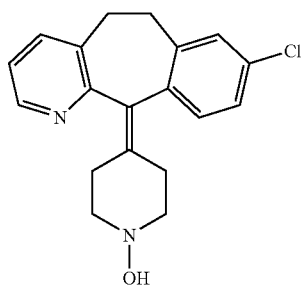
V

CHART 1(continued)

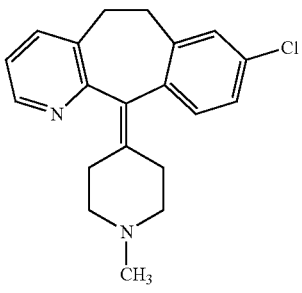
VI

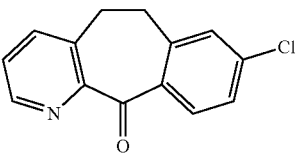
VII

What is claimed is:

1. A solid composition comprising: (1) an immediate release layer comprising an anti-allergic effective amount of desloratadine and a desloratadine-protective amount of two pharmaceutically acceptable antioxidants; and (2) a sustained release layer comprising an effective amount of pseudoephedrine or a pharmaceutically acceptable salt thereof and a pharmaceutically acceptable sustained release agent; wherein the total amount of desloratadine degradation products in the solid composition is less than or equal to about 2% by weight, and wherein at least about 80% of the desloratadine dissolves in a 0.1N HCl solution at 37° C. in about 45 minutes.

2. The solid composition of claim 1 wherein the two pharmaceutically acceptable antioxidants are edetate disodium and citric acid.

3. A solid composition comprising: (1) an immediate release first layer comprising an anti-allergic effective amount of desloratadine and at least one pharmaceutically acceptable antioxidant; and (2) a sustained release second layer comprising an effective amount of pseudoephedrine or a pharmaceutically acceptable salt thereof and a pharmaceutically acceptable sustained release agent; wherein the total amount of desloratadine degradation products in the solid composition is less than or equal to about 2% by weight, and wherein at least about 80% of the desloratadine dissolves in a 0.1N HCl solution at 37° C. in about 45 minutes.

4. A solid composition comprising: (1) an immediate release first layer comprising about 2.5 mg of desloratadine and a desloratadine-protective amount of at least one pharmaceutically acceptable antioxidant; (2) a sustained release second layer comprising about 120 mg of pseudoephedrine or a pharmaceutically acceptable salt thereof; and (3) a pharmaceutically acceptable excipient, wherein at least about 80% of the desloratadine dissolves in a 0.1N HCl solution at 37° C. in about 45 minutes.

5. The solid composition of claim 4 wherein the total amount of desloratadine degradation products is less than or equal to about 2% by weight.

6. The solid composition of claim 4 wherein a desloratadine-protective amount of a pharmaceutically acceptable binder is present in the sustained release second layer.

7. The solid composition comprising a first and a second layer wherein the first layer is an immediate release layer comprising:

| INGREDIENT | mg/composition |
| --- | --- |
| Desloratadine, micronized | 5.0 |
| Corn Starch | 36.0 |
| Microcrystalline Cellulose | 140.7 |
| Edetate Disodium | 10.0 |
| Citric Acid | 2.0 |
| Talc | 6.0 |
| Dye | 0.30 |
| TOTAL | 200.00 | and wherein the second layer is a sustained release layer comprising:

| INGREDIENT | mg/composition |
| --- | --- |
| Pseudoephedrine Sulfate | 120.0 |
| Hydroxypropyl Methylcellulose 2208, 100,000 cps | 105.0 |
| Microcrystalline Cellulose | 103.5 |
| Hydroxypropyl Methylcellulose 2910 | 10.5 |
| Edetate Disodium | 3.5 |
| Silicon Dioxide | 5.0 |
| Magnesium Stearate (Non-Bovine) | 2.5 |
| TOTAL | 350.0 |
| TOTAL Tablet Weight | 550.0 | wherein the total amount of desloratadine degradation products in the solid composition is less than or equal to about 2% by weight.

8. A solid composition comprising a first layer and a second layer, wherein the first layer is an immediate release first layer comprising:

| INGREDIENT | mg/composition |
| --- | --- |
| Desloratadine, micronized | 2.5 |
| Corn Starch | 18.0 |
| Microcrystalline Cellulose | 71.22 |
| Edetate Disodium | 5.0 |

-continued

| INGREDIENT | mg/composition |
|---|---|
| Citric Acid | 1.0 |
| Talc | 3.0 |
| Dye | 0.28 |
| TOTAL | 100.00 | and wherein the second layer is a sustained release layer comprising:

| INGREDIENT | mg/composition |
|---|---|
| Pseudoephedrine Sulfate | 120.0 |
| Hydroxypropyl Methylcellulose 2208 | 105.0 |
| Microcrystalline cellulose | 103.5 |
| Edetate Disodium | 3.5 |
| Hydroxypropyl Methylcellulose 2910 | 10.5 |
| Silicon Dioxide | 5.0 |
| Magnesium stearate | 2.5 |
| TOTAL | 350.0 | and wherein total amount of desloratadine degradation products in the solid composition is less than or equal to about 2% by weight.

9. The solid composition of claim 8 wherein at least about 80% of the desloratadine dissolves in a 0.1N HCl solution at 37° C. in about 45 minutes.

10. A method of treating allergic or inflammatory conditions of the upper and lower airway passages and skin which comprises administering to a patient in need of such treating an effective amount of the solid composition of claim 1.

11. A method of treating the signs and symptoms of nasal congestion associated with allergic and inflammatory conditions of the upper or lower airway passages and skin which comprises administering to a patient in need of such treating an effective amount of the solid composition of claim 1.

12. A method of treating the signs and symptoms of nasal congestion associated with allergic or inflammatory conditions of the upper and lower airway passages and skin which comprises administering to a patient in need of such treating an effective amount of the solid composition of claim 3.

13. A method of treating the signs and symptoms of nasal congestion associated with allergic or inflammatory conditions of the upper and lower airway passages and skin which comprises administering to a patient in need of such treating an effective amount of the solid composition of claim 4.

14. A method of treating the signs and symptoms of nasal congestion associated with allergic or inflammatory conditions of the upper and lower airway passages and skin which comprises administering to a patient in need of such treating an effective amount of the solid composition of claim 8.

15. A method of treating the signs and symptoms of urticaria which comprises administering to a patient in need of such treating an effective amount of the solid composition of claim 1.

16. A method of treating the signs and symptoms of urticaria which comprises administering to a patient in need of such treating an effective amount of the solid composition of claim 3.

17. A method of treating the signs and symptoms of urticaria which comprises administering to a patient in need of such treating an effective amount of the solid composition of claim 4.

18. A method of treating the signs and symptoms of urticaria which comprises administering to a patient in need of such treating an effective amount of the solid composition of claim 7.

19. A method of treating the signs and symptoms of urticaria which comprises administering to a patient in need of such treating an effective amount of the solid composition of claim 8.

20. A method of treating the nasal and non-nasal symptoms of perennial or seasonal allergic rhinitis which comprises administering to a patient in need of such treating an effective amount of the solid composition of claim 1.

21. A method of treating the nasal and non-nasal symptoms of perennial or seasonal allergic rhinitis which comprises administering to a patient in need of such treating an effective amount of the solid composition of claim 3.

22. A method of treating the nasal and non-nasal symptoms of perennial or seasonal allergic rhinitis which comprises administering to a patient in need of such treating an effective amount of the solid composition of claim 4.

23. A method of treating the nasal and non-nasal symptoms of perennial or seasonal allergic rhinitis which comprises administering to a patient in need of such treating an effective amount of the solid composition of claim 7.

24. A method of treating the nasal and non-nasal symptoms of perennial or seasonal allergic rhinitis which comprises administering to a patient in need of such treating an effective amount of the solid composition of claim 8.

25. A method of treating allergic or inflammatory conditions of the upper and lower airway passages and skin which comprises administering to a patient in need of such treating an effective amount of the solid composition of claim 3.

26. A method of treating allergic or inflammatory conditions of the upper and lower airway passages and skin which comprises administering to a patient in need of such treating an effective amount of the solid composition of claim 4.

27. A method of treating allergic or inflammatory conditions of the upper and lower airway passages and skin which comprises administering to a patient in need of such treating an effective amount of the solid composition of claim 7.

28. A method of treating allergic or inflammatory conditions of the upper and lower airway passages and skin which comprises administering to a patient in need of such treating an effective amount of the solid composition of claim 8.

29. A method of treating the signs and symptoms of nasal congestion associated with allergic and inflammatory conditions of the upper or lower airway passages and skin which comprises administering to a patient in need of such treating an effective amount of the solid composition of claim 7.

* * * * *